(12) United States Patent
Genthe

(10) Patent No.: US 7,993,930 B2
(45) Date of Patent: Aug. 9, 2011

(54) METHOD AND DEVICE FOR DETERMINING THE PHOSPHORUS CONTENT OF AN AQUEOUS SAMPLE

(75) Inventor: Wolfgang Genthe, Berlin (DE)

(73) Assignees: Lar Process Analysers AG, Berlin (DE); Werner Arts, Berlin (DE)

( * ) Notice: Subject to any disclaimer, the term of this patent is extended or adjusted under 35 U.S.C. 154(b) by 0 days.

(21) Appl. No.: 12/524,893

(22) PCT Filed: Jan. 29, 2008

(86) PCT No.: PCT/EP2008/051064
§ 371 (c)(1),
(2), (4) Date: Mar. 5, 2010

(87) PCT Pub. No.: WO2008/092869
PCT Pub. Date: Aug. 7, 2008

(65) Prior Publication Data
US 2010/0173419 A1   Jul. 8, 2010

(30) Foreign Application Priority Data

Jan. 29, 2007 (DE) .......................... 10 2007 004 339

(51) Int. Cl.
*G01N 31/12* (2006.01)
*G01N 31/00* (2006.01)
*G01N 21/00* (2006.01)

(52) U.S. Cl. ........... 436/103; 422/78; 422/80; 422/68.1; 422/50

(58) Field of Classification Search .................. 436/103; 422/78, 80, 68.1, 50
See application file for complete search history.

(56) References Cited

U.S. PATENT DOCUMENTS

| | | | | |
|---|---|---|---|---|
| 3,607,070 A | * | 9/1971 | Stenger et al. | 436/103 |
| 5,270,216 A | * | 12/1993 | Kan et al. | 436/103 |
| 5,702,954 A | | 12/1997 | Stedman et al. | |
| 6,177,276 B1 | * | 1/2001 | Richardson et al. | 436/55 |
| 2003/0032194 A1 | | 2/2003 | Wreyford | |
| 2008/0026482 A1 | * | 1/2008 | Arts et al. | 436/114 |

FOREIGN PATENT DOCUMENTS

| | | |
|---|---|---|
| DE | 4344441 | 7/1995 |
| DE | 10240410 | 2/2004 |
| EP | 0684471 | 11/1995 |
| EP | 0634646 | 1/1999 |
| EP | 0887643 | 5/2002 |
| EP | 1055927 | 10/2004 |
| JP | 2728706 | 1/1979 |
| JP | 59154358 | 9/1984 |
| JP | 61140836 | 6/1986 |
| JP | 07027706 | 1/1995 |
| JP | 2004093509 | 3/2004 |
| WO | WO 2005/064329 | * 7/2005 |

* cited by examiner

*Primary Examiner* — Walter D Griffin
*Assistant Examiner* — Christine T Mui
(74) *Attorney, Agent, or Firm* — Volpe And Koenig, P.C.

(57) ABSTRACT

Method for determining the phosphorus content of an aqueous sample, in particular drainage-water sample, wherein the sample is subjected to thermal-oxidative decomposition and the orthophosphate content of the decomposed sample is determined photometrically in an aqueous analysis solution, such that the thermal decomposition is carried out in a single step by catalyzer-free burning of the sample as batch-decomposition in a combustion oven, the resulting combustion gas is transferred out of the combustion oven in a carrier-gas stream and the combustion/carrier gas stream is cooled to obtain the aqueous analysis solution as a condensate therefrom.

19 Claims, 3 Drawing Sheets

METHOD AND DEVICE FOR DETERMINING THE PHOSPHORUS CONTENT OF AN AQUEOUS SAMPLE

BACKGROUND

The invention relates to a method for determining the phosphorus content of an aqueous sample, as well as to an apparatus with which to implement the method.

A known way to determine the amount of particular substances contained in water—and hence the quality of the water and in particular of drainage water contaminated with organic materials, nitrogen compounds and/or halogen compounds—is to vaporize a sample in an atmosphere comprising a transport gas (carrier gas) enriched with oxygen and burn it, and to deliver the gas mixture obtained by this combustion to a detector suitable for demonstrating the presence of carbon dioxide, nitrogen oxides and the like.

As detectors the following (among others) have proved useful: infrared detectors for the carbon content, special chemoluminescence detectors or electrochemical sensors for the nitrogen content, and so-called coulometric detectors for the halogenide content.

The detection methods based on the combustion of a water sample have been widely used to determine the sample's content of organic substances, the so-called TOC (total organic carbon). For this purpose a small amount of the water with the transport gas is customarily placed in an oven heated to a preset temperature by resistance heating; here it is almost immediately vaporized and burnt, and the resulting gas is sent to an NDIR-$CO_2$ detector, which signals a $CO_2$ content that indicates the C content of the water sample. A more advanced embodiment of this procedure and a corresponding apparatus are described in DE 43 44 441 C2. A modified arrangement for measuring very low TOC values—for instance in extremely clean water or very pure solutions for medical applications is described in EP 0 684 471 A2.

Further developed methods of this kind and appropriately designed reactors or complete arrangements have been proposed by the applicant in EP 0 887 643 B1 and EP 1 055 927 B1.

In addition to the above-mentioned materials contained in water, phosphorus is also a chemical element which can substantially affect the quality of drainage water and the techniques needed to process such water, depending on the amount present; for some time, therefore, increased attention has been directed to its quantitative measurement. Unlike the water contents carbon, nitrogen and halogenides, phosphorus has not thus far been quantitatively demonstrable in a gaseous medium (combustion gas+carrier gas). Instead, detection methods that have proved useful for this purpose are implemented with an aqueous solution. These methods employ, to put it simply, the change in colour of an aqueous sample to which a special reagent has been added; they are known as "blue method" or "yellow method" and are specified in corresponding standards.

Whereas phosphorus occurs in natural water in three fractions, namely as (1) inorganic, dissolved orthophosphate, (2) dissolved organic phosphorus compounds and (3) particulate phosphorus bound to biomasses or attached to particles, the known demonstration methods are based on measurement of the orthophosphate content. In order to determine the entire phosphorus content of an aqueous sample, therefore, an assessment of fractions (2) and (3) is needed, by converting them to photometrically detectable orthophosphate.

For this conversion a method has long been known that employs oxidation with addition of chemicals in an acidic medium, in some cases with increased pressure and an elevated reaction temperature; cf. for instance JP 2004093509 A. A known means of determining the phosphorus content in an organic material (e.g., oil) is to mix this material with an alkaline solution and burn it under oxygen atmosphere in a hermetically sealed reaction vessel; cf. JP 62003643 A.

The U.S. Pat. No. 5,702,954 describes a several-step procedure for analysis of plant or animal phosphate-containing samples, which includes combustion in the presence of a reduction means (e.g., hydrogen) followed by conversion with ozone in another reaction chamber at ambient temperature. US 2003/0032194 A1 also describes a several-step oxidation method which was developed primarily for detecting nitrogen and sulphur, but also phosphorus, in a sample containing these elements. Thermal decomposition methods employing special catalyzers or ozone are also known, for example, from JP 59154358 A or JP 61140836 A.

Various other known methods make use of photo-oxidative decomposition of the sample under LTV radiation, in particular in the presence of a photo-oxidation catalyzer. Methods of this kind are described, e.g., in EP 0 634 646 B1 or JP 07027706 A.

SUMMARY

The objective of the present invention is to provide an improved method and an improved apparatus for determining the amount of phosphorus in an aqueous sample, which allow an analysis of the samples that uses uncomplicated technology and less consumable material, so that it is more economical, and can easily be carried out in practice.

This objective is achieved in its methodological aspect by a method according to the invention, and with regard to the equipment by an apparatus with the features of the invention. Advantageous further developments of the idea underlying the invention are presented in the dependent claims.

The invention includes the substantial, and surprising, idea of carrying out the decomposition of a sample—that is, converting the various phosphorus fractions into photometrically demonstrable orthophosphate—in a single step and without a catalyzer, by burning the sample in a combustion oven (i.e. in the presence of oxygen). This combustion is performed as a batch-decomposition, i.e. by introducing a predetermined small amount of the sample into the (otherwise hermetically sealed) oven in an injection process.

Furthermore, the invention includes the idea of guiding the combustion gas thus produced away from the combustion oven within a stream of carrier gas and cooling this gas stream, in order to obtain the aqueous solution needed for analysis, in such a way that the condensate separated from the gas stream contains essentially the entire phosphorus content of the sample in the form of orthophosphate.

The invention provides the substantial advantages of a method that is simple and easily controllable from the outset, is implemented with a small number and amount of consumables (chemical substances employed), and is classifiable as advantageous with respect to working and environmental-protection aspects.

In one advantageous embodiment of the method the decomposed sample is used not only to determine its phosphorus content, but also to determine the content of other substances, in particular carbon and/or nitrogen. For this purpose it is sent to a suitable detector in each case, i.e. a $CO_2$ detector constructed as usual (NDIR detector) to determine carbon, and a conventional NO detector (chemoluminescence detector or electrochemical sensor) to determine nitrogen.

The combustion-carrier gas stream used here can be the same as that withdrawn from the condensate to make available the aqueous solution for analysis. In an alternative way of implementing the method, however, a variety of samples and associated decomposition procedures can be provided, on the one hand for determining phosphorus and on the other for determining C/N. A special implementation can comprise an alternating P and C/N determination for sequential thermally decomposed measurement samples.

In another embodiment of the invention it is provided that the condensate is collected in a cooling trap, from which a specified amount is withdrawn for photometric detection. An especially variable design, which is well suited for manipulation of small sample quantities, provides that the withdrawal of condensate from the cooling trap and its transport to a detection site are performed by means of an injection syringe, in particular one that is coordinate-controlled and/or motor-actuated.

The employment of an injection syringe has the added advantage that it also enables the withdrawn condensate to be mixed with the chemical reagent with which it must be combined for photometric detection, in that the reagent is simply drawn into the syringe after the condensate and, if necessary, mixed with the condensate by multiple actuation of the piston. It is useful for the aqueous analysis-solution then to be transferred to a flow-through cuvette in order to carry out one of the known analysis procedures. Alternatively, the condensate can also be injected into a stream of reagent.

The crucial step of cooling the combustion/carrier gas stream can be carried out precisely, and under simple electrical control, by means of a Peltier cooler. Furthermore, it can be provided that the combustion/carrier gas stream is cooled in two stages, in the first of which the condensate is obtained and in the second, it is cooled to a temperature near 0° C. (approximately 2-4° C.).

With regard to the apparatus, the invention incorporates the substantial idea of providing, downstream from a conventionally constructed combustion oven, a gas cooler with cooling trap for separating the condensate from the combustion/carrier gas stream, as well as means with which to extract the condensate from that trap and transport it to a P-detection site (a photometric detection device). It follows from this that the combustion oven is provided with suitable means for making available and introducing a carrier gas and a sample, as well as a connection between oven outlet and gas cooler, and that the apparatus finally also comprises a photometric phosphorus-detection device.

In a useful embodiment of this apparatus it is provided that the gas cooler comprises two cooling stages, such that the cooling trap is associated with the first cooling stage. The apparatus is particularly simple, and easy to control and handle, in an embodiment such that the gas cooler and/or at least one cooling stage is implemented as an electrically T-controllable Peltier cooler.

An advantageous embodiment of the condensate-transporting device is characterized in that it comprises a coordinate-controlled and/or stepping motor-driven injection syringe. In this case the cooling trap and the condensate-transporting device are usefully adapted to one another in such a way that the injection syringe is dipped from above into a condensate reservoir (which is of course accessible from above). The sample can also be introduced to the combustion oven in the same way, i.e. with an injection-syringe device that injects the water or drainage-water sample from above.

Moreover, in one embodiment of the invention the combustion oven is designed as a hermetically sealable vertical oven, such that the carrier gas and sample are introduced to the oven's upper region, and the conduit for removing the combustion/carrier gas is disposed in its lower region. This sealability is ensured by the provision of appropriate valves in the conduits for introducing the sample and carrier gas as well as the conduit for gas removal.

In another embodiment of the invention the proposed apparatus comprises, in addition to the means for determining phosphorus content, a $CO_2$ detector for determining carbon content and/or an NO detector for determining nitrogen content, each of which is disposed at a gas outlet of the gas cooler.

BRIEF DESCRIPTION OF THE DRAWINGS

Further advantages and useful features of the invention will be apparent from the following description of an exemplary embodiment and substantial aspects of this embodiment with reference to the figures. These show the following.

DETAILED DESCRIPTION OF THE PREFERRED EMBODIMENTS

Figure 1:
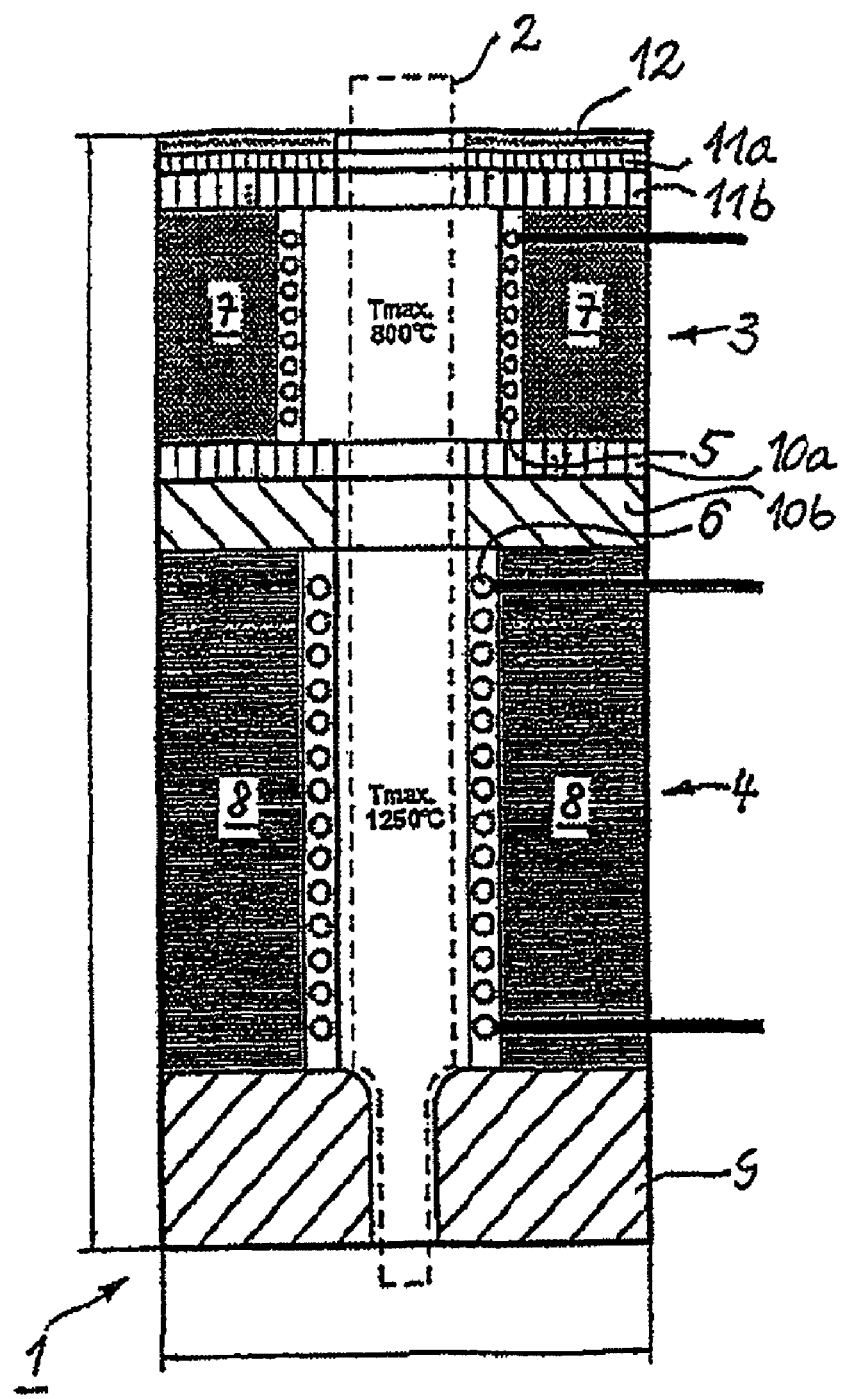
FIG. 1 a schematic cross-sectional illustration of the main sections of a combustion oven in an apparatus according to one embodiment of the invention, FIG. 2 a sketch-like overall illustration of an apparatus in accordance with the invention, and FIG. 3 a cross-sectional illustration of the central components of the gas-liquid separator (gas cooler) in the apparatus shown in FIG. 2.

FIG. 1 shows a schematic cross section through the most important parts of a sample-combustion oven 1 in an embodiment suitable for implementing the method in accordance with the invention, into which a substantially elongated cylindrical ceramic reaction vessel 2 (the outline of which is represented in the figure by a dashed line) can be set. This has at its lower end (cold end of the oven) a tubular outlet with a diameter in the range between 6 and 10 mm, which can easily be cleaned from below in order to remove salt deposits.

The oven 1 comprises a first, upper heating zone 3, in which according to this embodiment a maximal temperature of 800° C. can be reached, and a second, lower heating zone 4 in which the maximal temperature is 1250° C. The two heating zones are heated by means of heating wires 5, 6 in the form of hollow cylinders made of a special high-temperature-resistant alloy, namely the material Kanthal-Fibrothal®, which are disposed around the respective section of the reaction vessel 2. The upper and the lower heating zones comprise ceramic-fibre insulators 7 and 8, which differ in thickness because of the different maximal temperatures; the foot region, i.e. the region 10a, 10b between the heating zones, and the region 11a, 11b below an aluminium cover 12 are also insulated by ceramic fibres. A device (not shown in the figure) for charging with the sample and supplying carrier gas is also provided, in the region above the cover 12.

The oven construction shown in FIG. 1 and described above advantageously enables the long-term production of high temperatures, generated especially in the second, lower heating zone 4, while the special insulation both contributes to a tolerable energy consumption and eliminates potential danger to the surroundings.

An aqueous sample introduced into this combustion oven is decomposed by catalyzer-free combustion at no less than 1200° C., preferably about 1250° C., in such a way that the various phosphorus fractions it contains are all converted to orthophosphate and are thus made accessible for demonstration by the known and standardized demonstration methods (in particular blue and yellow methods), as has been confirmed by the inventor.

Figure 2:
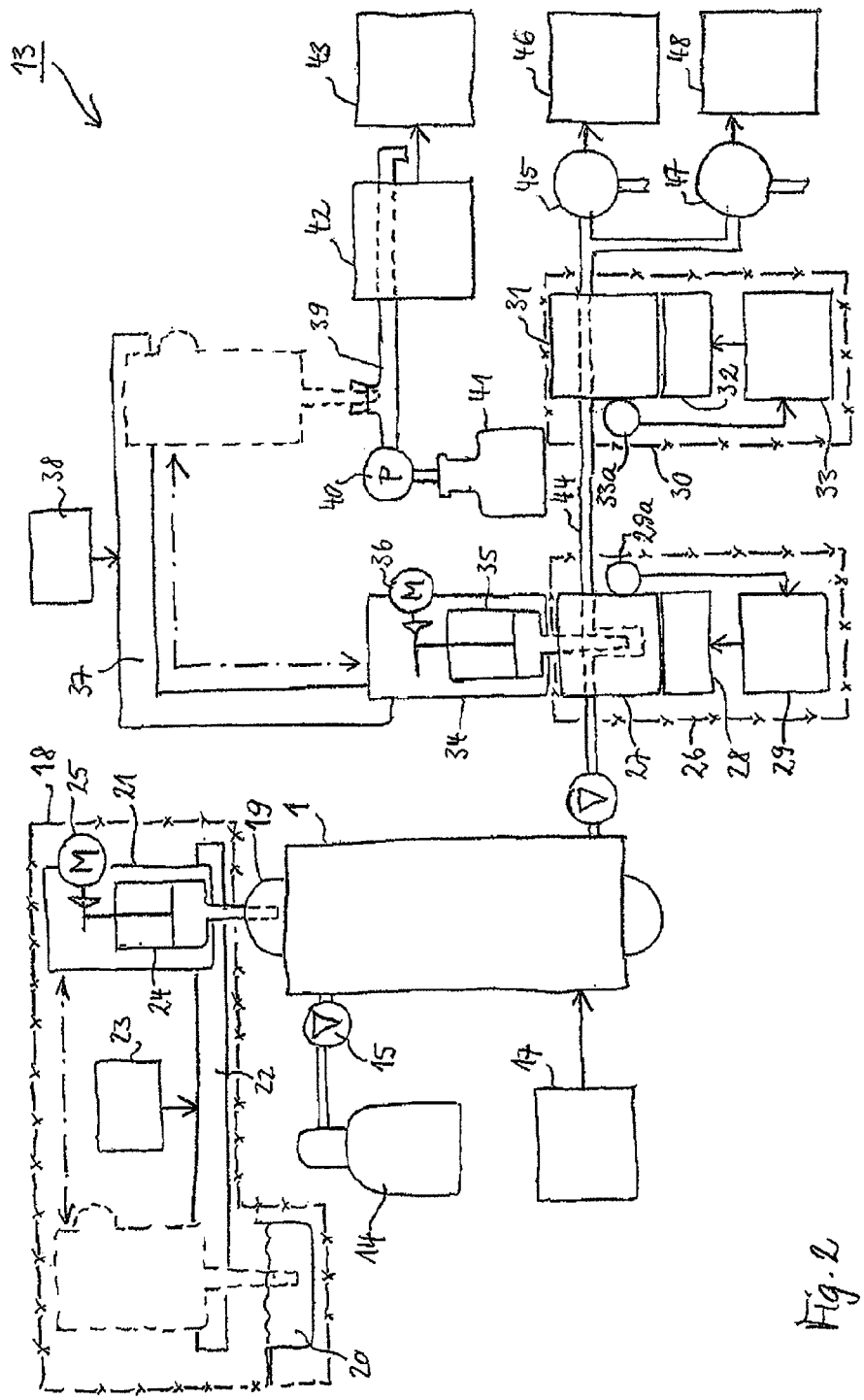

FIG. 2 is a sketch to show in principle the overall construction of a measurement apparatus 13 for determining the various substances contained in drainage water or water intended for use. As the main component of this apparatus 13, the combustion oven 1 illustrated in FIG. 1 and described above is shown; alternatively, however, another type of combustion oven (possibly with radiant heating) can occupy this position. For the sake of better clarity parts not essential to the invention, such as might serve for calibration and cleaning of the measurement apparatus, have been omitted from this sketch-like representation.

Likewise not shown is a controlling unit (controller), which controls the entire sequence of events comprising the sample decomposition and measurement processes, and for this purpose is of course connected to the main blocking, transport, heating and demonstration devices in this apparatus. The implementation and operation of such a control device, on the basis of the procedural description given here and the construction of the apparatus as explained below, is within the scope of a person skilled in the art.

Associated with the combustion oven 1, as a core item in the measurement apparatus 13, on the input side there is a carrier-gas storage container 14 to provide carrier gas for the measurement processes, with attached thereto the input-valve device 15. In addition, the oven has a heating-control unit 17 to control the electrical heating of the oven, and a sample-feeding device 18 to feed the sample into a sample-injection valve 19 of the oven.

The sample-feeding device 18 comprises a sample reservoir 20, such as can be disposed for example at the inlet of a clarification plant, an injection unit 21, which is transportably mounted on a carrier 22, and an associated transport controller 23. The syringe unit 21 comprises a dosing syringe 24 and a stepping motor 25 to achieve precisely controllable actuation of the syringe and hence the dosage of a predetermined sample volume.

At the outlet of the oven 1 a first cooling stage 26 is disposed, which comprises a cooling-trap unit 27, a Peltier cooler 28 and an associated temperature controller 29 with T-sensor 29a at or in the cooling-trap unit 27. Downstream from the first cooling stage 26 is a second cooling stage 30, which comprises a cooling block 31 with associated Peltier cooler 32 and, to control the latter, a temperature-control unit 33 with T-sensor 33a.

At the first cooling stage 26 is disposed another syringe unit 34 which in analogy to the syringe unit 21 for supplying the combustion oven 1 comprises an injection syringe 35 with stepping motor 36 for its precisely controlled actuation. In addition, this syringe unit 34 is likewise mounted on a transport carrier 37, with which is associated a transport-control unit 38 for transporting the syringe unit into a second operating position. The latter is above a flow-through cuvette 39, into which the needle of the injection syringe 35 can be inserted, as into the cooling trap 27. This second operating position is indicated by a dashed line, as is the initial operating position of the syringe unit 21.

Attached to an input of the flow-through cuvette 39, by way of a pump 40, is a reagent container 41 in which a chemical needed for the photometric phosphorus detection is stored. The flow-through cuvette 39 projects into a photometer unit 42 which is designed for photometric analysis of an aqueous sample flowing through the flow-through cuvette 39, and the outlet of which is connected to a phosphorus-evaluation stage 43.

At the outlet of the second cooling stage 30 the output conduit 44 of the combustion oven 1 divides into two branches, one leading to an NO detector 45 which on its outlet side is connected to a nitrogen (TN) evaluation stage 46, and the other to a $CO_2$ detector 47 which on its outlet side is connected to a carbon (TOC) evaluation stage 48.

The way the measurement apparatus 13 functions will already be largely evident from the above explanations of the method in accordance with the invention, but is again briefly summarized as follows.

By means of the first syringe unit 21 an aqueous sample is taken out of the reservoir 20, transported to the combustion oven 1 and injected into the oven. At the temperatures to which the interior has been set, the sample is vaporized and burned almost instantaneously, and the resulting combustion gas is transported from the oven into the output conduit 44, along with a carrier-gas stream supplied by the carrier-gas reservoir 14. In the condenser the combustion/carrier gas stream is cooled down to a first cooling temperature, at which a condensate is formed in the cooling trap 27. A predetermined amount of this condensate is withdrawn by means of the second syringe unit 34 and is placed in the flow-through cuvette 39, where it is mixed with the reagent provided by the pump 40 in order to enable a photometric detection process, and is then sent to the photometer unit 42 for phosphorus detection.

In the second cooling stage 30 the combustion/carrier gas stream is cooled to a second cooling temperature near 0° C., and at the output side of the cooling stage the gas is sent to the detectors 45 and 47 for the demonstration of NO and $CO_2$. When the demonstration processes in the detectors 42, 45 and 47 have produced results, the respective evaluation stages 43, 46 and 48 determine the total phosphorus content (TP), the total nitrogen content (TN) and the total content of organic carbon (TOC) of the aqueous sample that was taken from the reservoir 20 and decomposed in the combustion oven 1.

Figure 3:
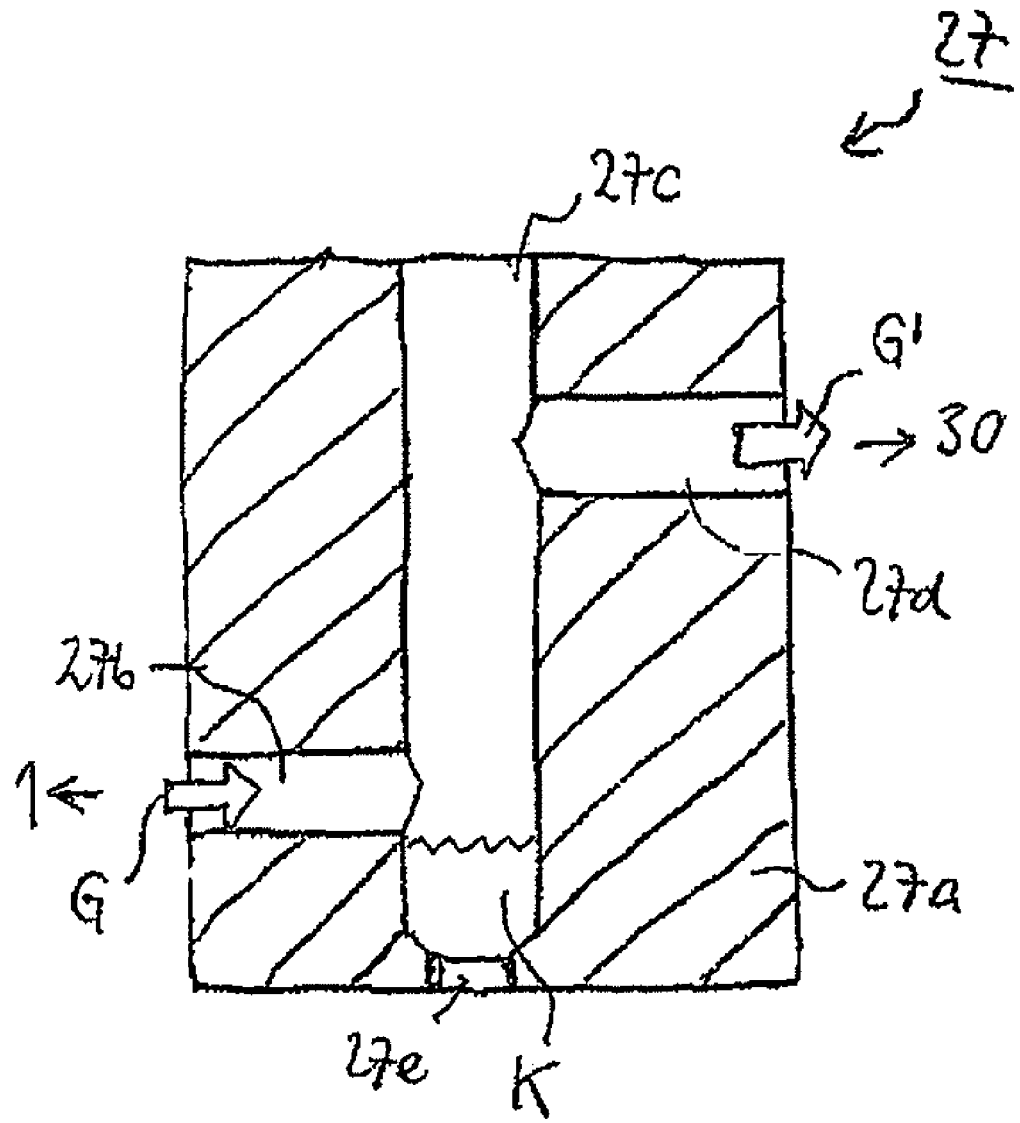

FIG. 3 shows the structure of the cooling trap 27 in greater detail, in a cross-sectional drawing. In a block 27a representing the basic body an input section 27b has been constructed, by way of which the cooling trap 27 is in communication with the output of the combustion oven 1, and through which a combustion/carrier gas stream G enters. The input section 27b opens into a vertical bore 27c, in the lower region of which during cooling of the gas stream a condensate K is deposited. In the upper region of the basic body 27a an additional horizontal passage section 27d is provided, which opens into the bore 27c and by way of which the cooled and condensate-free combustion/carrier gas stream G' is finally guided to the second cooling stage 30. A plug 27e closes the lower end of the bore 27c.

The embodiment of the invention is not limited to the example explained above and the aspects emphasized here, but is also possible in a large number of modifications that are within the scope of a person skilled in the art. In particular the two-stage cooling arrangement described can be replaced by a simple, single-stage gas-liquid separator, and also with respect to the sample-supply arrangement employing the first syringe unit and/or to the mounting and transport of the second syringe unit simplifications are possible in the interest of cost reduction, in particular by elimination of the associated electronically controlled transport mechanism.

The invention claimed is:

1. Method for determining phosphorus content of an aqueous sample, comprising; subjecting the sample to thermal-oxidative decomposition and determining an orthophosphate content of the decomposed sample in aqueous analysis solution photometrically, the thermal oxidative decomposition is carried out in a single step by catalyzer-free burning of the sample as a batch-decomposition in a combustion oven, removing the resulting combustion gas from the combustion oven in a carrier-gas stream, and cooling the stream of combustion/carrier gas so as to obtain the aqueous analysis solution as a condensate therefrom.

2. Method according to claim 1, further comprising determining a carbon or nitrogen content of the sample by conducting the cooled combustion/carrier gas stream to at least one of a $CO_2$ or NO detector.

3. Method according to claim 2, wherein the determination of phosphorus content with reference to the aqueous analysis sample, and of the carbon or nitrogen contents of the sample from the combustion/carrier gas stream, are carried out separately with differently decomposed samples.

4. Method according to claim 2, wherein the determination of phosphorus content with reference to the aqueous analysis sample, and of the at least one of the carbon or nitrogen contents of the sample from the combustion/carrier gas stream, are carried out with one and the same decomposed samples.

5. Method according to claim 1, further comprising collecting the condensate in a cooling trap and withdrawing a specified amount therefrom for photometric detection.

6. Method according to claim 5, further comprising using an injection syringe for the withdrawal of the condensate from the cooling trap and transport of the condensate to a detection site.

7. Method according to claim 6, further comprising using the injection syringe for mixing of the withdrawn condensate with a liquid reagent to form the aqueous analysis solution.

8. Method according claim 1, wherein the aqueous analysis sample is transferred to a flow-through cuvette or to another detection unit for photometric detection.

9. Method according to claim 1, wherein the combustion/carrier gas stream is cooled by a Peltier cooler to a predetermined temperature.

10. Method according to claim 1, wherein the combustion/carrier gas stream is cooled in two stages, such that in a first stage the condensate is obtained and in a second stage cooling to nearly 0° C. occurs.

11. Apparatus for determining phosphorus content of an aqueous sample, wherein the sample is subjected to thermal-oxidative decomposition and orthophosphate content of the decomposed sample in aqueous analysis solution is determined photometrically, the apparatus comprising:

a thermal reactor which comprises a combustion oven with a carrier-gas inlet, a sample inlet and a combustion/carrier gas outlet, a carrier-gas source connected upstream to the combustion oven, a gas-liquid separator connected downstream to the combustion oven, to separate a condensate from the combustion/carrier gas stream, a condensate-transport device to withdraw condensate from a cooling trap and to transport it to a detection site, and a photometric phosphorus-detection device adapted to analyze the condensate.

12. Apparatus according to claim 11, further comprising a gas cooler that comprises two cooler stages, such that the cooling trap is associated with the first cooler stage.

13. Apparatus according to claim 12, wherein the gas cooler or at least one cooler stage is constructed as an electrically T-controllable Peltier cooler.

14. Apparatus according to claim 11, wherein the condensate-transport device comprises an injection syringe that is at least one of coordinate-controlled or driven by a stepping motor.

15. Apparatus according to claim 14, wherein the cooling trap comprises a condensate reservoir that is accessible from above, and the condensate-transport device is adapted to allow the injection syringe is inserted from above into the condensate reservoir.

16. Apparatus according to claim 11, wherein the combustion oven is a hermetically sealable vertical oven, and the carrier-gas inlet and sample inlet are in an upper region, and an outlet for combustion/carrier gas is disposed in a lower region of the oven.

17. Apparatus according to claim 11, wherein the sample inlet of the combustion oven comprises an injection syringe that is at least one of coordinate-controlled or driven by a stepping motor.

18. Apparatus according to claim 11, wherein the photometric phosphorus-detection device comprises a measurement cuvette, adapted to be filled by an injection syringe.

19. Apparatus according to claim 11, further comprising at least one of a $CO_2$ detector disposed at a gas outlet of the gas cooler to determine a carbon content or an NO detector to determine a nitrogen content.

* * * * *